US010420531B2

(12) United States Patent
Corl

(10) Patent No.: US 10,420,531 B2
(45) Date of Patent: Sep. 24, 2019

(54) SYNTHETIC APERTURE IMAGE RECONSTRUCTION SYSTEM IN A PATIENT INTERFACE MODULE (PIM)

(71) Applicant: Volcano Corporation, San Diego, CA (US)

(72) Inventor: Paul Douglas Corl, Palo Alto, CA (US)

(73) Assignee: VOLCANO CORPORATION, San Diego, CA (US)

( * ) Notice: Subject to any disclaimer, the term of this patent is extended or adjusted under 35 U.S.C. 154(b) by 710 days.

(21) Appl. No.: 14/137,304

(22) Filed: Dec. 20, 2013

(65) Prior Publication Data
US 2014/0187925 A1 Jul. 3, 2014

Related U.S. Application Data

(60) Provisional application No. 61/746,733, filed on Dec. 28, 2012.

(51) Int. Cl.
A61B 5/00 (2006.01)
A61B 8/08 (2006.01)
(Continued)

(52) U.S. Cl.
CPC .............. *A61B 8/12* (2013.01); *A61B 5/0066* (2013.01); *A61B 5/0084* (2013.01);
(Continued)

(58) Field of Classification Search
CPC ....... A61B 5/0084; A61B 8/12; G01T 11/003; H03K 19/17728
(Continued)

(56) References Cited

U.S. PATENT DOCUMENTS 4,683,893 A * 8/1987 Mayo .................. G01S 7/52036
600/442
6,241,675 B1 * 6/2001 Smith ...................... A61B 8/06
128/916
(Continued)

FOREIGN PATENT DOCUMENTS

JP 2010-512826 A 4/2010
WO 199728743 A1 8/1997
(Continued)

OTHER PUBLICATIONS

International Search Report and Written Opinion received in Patent Cooperation Treaty Application No. PCT/US2013/077009, dated Apr. 10, 2014, 10 pages.
(Continued)

Primary Examiner — Serkan Akar
Assistant Examiner — Vani Gupta

(57) ABSTRACT

A field programmable gate array (FPGA) circuit including a quadrature internal conditioning circuit is provided. The circuit having a buffer circuit; and a reconstruction engine circuit, wherein the reconstruction engine circuit includes: a circuit to measure a phase of a signal; and a flavor interpolation circuit; wherein: the circuit to measure the phase of a signal includes digitization points forming two complex numbers for each cycle of the center frequency of the signal. A system for collecting tissue images including a patient interface module (PIM); a pulse transmitter circuit; an analog to digital converter circuit; and an FPGA circuit as above; and a catheter having a sensing head is also provided. A method for using the above system to provide an image reconstruction is also provided.

17 Claims, 11 Drawing Sheets

(51) Int. Cl.
*A61B 8/12* (2006.01)
*G01S 15/89* (2006.01)
*H03K 19/177* (2006.01)

(52) U.S. Cl.
CPC .......... *A61B 8/0891* (2013.01); *A61B 8/5207* (2013.01); *G01S 15/892* (2013.01); *G01S 15/8997* (2013.01); *H03K 19/17728* (2013.01)

(58) Field of Classification Search
USPC ...................................................... 600/425
See application file for complete search history.

(56) References Cited

U.S. PATENT DOCUMENTS

| | | | |
|---|---|---|---|
| 6,592,520 B1 * | 7/2003 | Peszynski | A61B 8/12 600/437 |
| 6,673,015 B1 | 1/2004 | Glover | |
| 2002/0115931 A1 | 8/2002 | Strauss | |
| 2005/0203396 A1 * | 9/2005 | Angelsen | A61B 8/12 600/437 |
| 2005/0215893 A1 * | 9/2005 | Barnes | G01S 15/8925 600/437 |
| 2006/0052697 A1 | 3/2006 | Hossack et al. | |
| 2006/0094963 A1 | 5/2006 | Sumanaweera et al. | |
| 2007/0239001 A1 * | 10/2007 | Mehi | G01S 7/52017 600/437 |
| 2009/0054780 A1 * | 2/2009 | Yang | G03B 42/06 600/447 |
| 2009/0241958 A1 * | 10/2009 | Baker, Jr. | A61M 16/0051 128/204.23 |
| 2010/0030081 A1 * | 2/2010 | Masuzawa | A61B 8/4483 600/459 |
| 2010/0142781 A1 | 6/2010 | Walker et al. | |
| 2011/0087104 A1 | 4/2011 | Moore et al. | |
| 2012/0004537 A1 | 1/2012 | Tolkowsky | |
| 2012/0065511 A1 * | 3/2012 | Jamello, III | A61B 8/0883 600/443 |
| 2012/0108911 A1 * | 5/2012 | Drysdale | G06F 19/3418 600/300 |

FOREIGN PATENT DOCUMENTS

| | | |
|---|---|---|
| WO | 2006076409 A2 | 7/2006 |
| WO | WO 2006-107755 A2 | 10/2006 |

OTHER PUBLICATIONS

International Searching Authority/European Patent Office, "Communication—Supplementary European Search Report," for European Application No. 13868858.5, dated Jul. 21, 2016, 9 pages.
Weibao Qiu et al: "An FPGA-based open platform for ultrasound biomicroscopy", IEEE Transactions on Ultrasonics, Ferroelectronics and Frequency Control IEEE, US, vol. 59, No. 7, Jul. 2, 2012, 11 pages.
Gronningsaeter A. et al: "Vessel wall detection and blood noise reduction in intravascular ultrasound imaging", IEEE Transactions on Ultrasonics. Ferroelectronics and Frequency Control, IEEE, US, vol. 43, No. 3, May 2, 1996, 11 pages.

* cited by examiner

SYNTHETIC APERTURE IMAGE RECONSTRUCTION SYSTEM IN A PATIENT INTERFACE MODULE (PIM)

CROSS-REFERENCE TO RELATED APPLICATIONS

The present application claims priority to and the benefit of U.S. Provisional Patent Application No. 61/746,733, filed Dec. 28, 2012, which is hereby incorporated by reference in its entirety.

TECHNICAL FIELD

The present disclosure relates generally to intravascular ultrasound (IVUS) imaging inside the living body and, in particular, to an IVUS Patient Interface Module (PIM) that provides an image from data collected with a solid state catheter including an array of ultrasound transducers.

BACKGROUND

Intravascular ultrasound (IVUS) imaging is widely used in interventional cardiology as a diagnostic tool for a diseased vessel, such as an artery, within the human body to determine the need for treatment, to guide the intervention, and/or to assess its effectiveness. IVUS imaging uses ultrasound echoes to create an image of the vessel of interest. The ultrasound waves pass easily through most tissues and blood, but they are partially reflected from discontinuities arising from tissue structures (such as the various layers of the vessel wall), red blood cells, and other features of interest. The IVUS imaging system, which is connected to the IVUS solid state catheter by way of a patient interface module (PIM), processes the received ultrasound echoes to produce a cross-sectional image of the vessel where the solid state catheter is placed.

Existing solid state IVUS catheters deliver useful diagnostic information at the cost of high system complexity, including a broad bandwidth requirement for data acquisition, high memory storage for buffering large amounts of data, and heavy computational requirements. Thus, there is a need for enhanced image quality to provide more valuable insight into the vessel condition, using a simplified system.

Accordingly, there remains a need for improved devices, systems, and methods for providing a compact and efficient circuit architecture and electrical interface to a solid state IVUS catheter used in an intravascular ultrasound system.

SUMMARY

According to embodiments disclosed herein a reconstruction field programmable gate array (FPGA) circuit may include a quadrature internal conditioning circuit; a buffer circuit; and a reconstruction engine circuit, wherein the reconstruction engine circuit includes: a circuit to measure a phase of a signal; and a flavor interpolation circuit; wherein: the circuit to measure the phase of a signal includes digitization points forming two complex numbers for each cycle of the center frequency of the signal.

According to embodiments disclosed herein a system for collecting tissue images may include a patient interface module (PIM), the PIM including: a pulse transmitter circuit; an analog to digital converter circuit; a reconstruction FPGA circuit; and a catheter having a sensing head near the distal end, the sensing head comprising an array of transducer elements, wherein the reconstruction FPGA circuit includes a quadrature internal conditioning circuit; a buffer circuit; and a reconstruction engine circuit, wherein the reconstruction engine circuit includes: a circuit to measure a phase of a signal; and a flavor interpolation circuit; wherein the circuit to measure the phase of a signal includes digitization points forming two complex numbers for each cycle of a center frequency of the signal.

According to some embodiments a method for image reconstruction may include receiving a signal from a plurality of transducers; processing the signal in an analog to digital converter; arranging data points in complex pairs; adjusting a phase of the complex pairs using an accumulator; and interpolating complex data points between flavors.

These and other embodiments of the present disclosure will be described in further detail below with reference to the following drawings.

BRIEF DESCRIPTION OF THE DRAWINGS

In the figures, elements having the same reference number have the same or similar functions.

DETAILED DESCRIPTION

Figure 1:
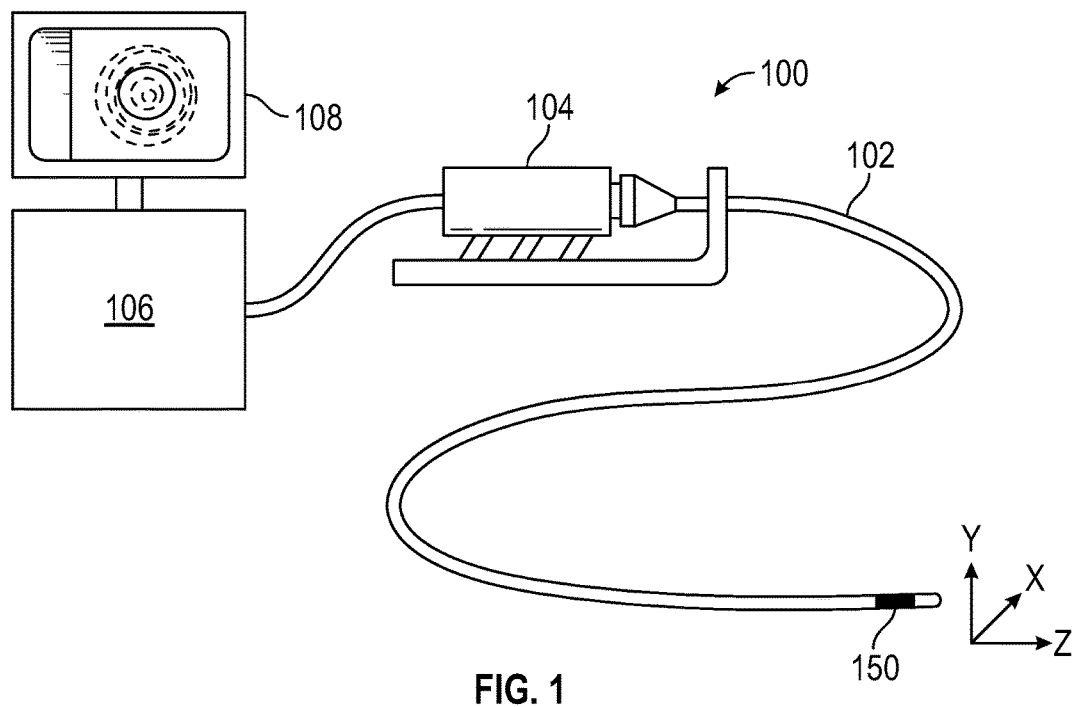
FIG. 1 is a diagrammatic schematic view of an imaging system according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure, as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In an IVUS solid state catheter consistent with embodiments disclosed herein, multiple ultrasound transducers are located around a sensing head. A solid state catheter or a solid state Patience-Interface-Module (PIM) as disclosed herein is understood as a catheter or a PIM that does not require physical rotation of a transducer to facilitate imaging. Further according to some embodiments, a solid state component such as a solid state catheter or a solid state PIM may include components made of a single piece, with no parts that may be separable or replaceable independently of one another. The sensing head is placed at the distal end of the catheter, near the tip of a flexible driveshaft. In some embodiments, the driveshaft may be inside a plastic sheath inserted into the vessel of interest. The plastic sheath protects the vessel tissue from wires inside the catheter, and permits ultrasound signals to freely propagate from the sensing head into the tissue, and back. A group of ultrasound transducers adjacent to each other may form a synthetic aperture when the transducers are stimulated in a fixed phase relative to one another. The synthetic aperture lies on a side portion of the sensing head, facing outwardly in a radial direction from the longitudinal axis of the catheter. The transducers listen for the returning echoes reflected from various tissue structures at each point where a collection of ultrasound beams having different focal depths has been launched. This forms an A-scan in the IVUS image. By sequentially selecting adjacent groups of transducers or apertures, the entire circumference of the sensing head may be covered, collecting A-scans around the catheter. Thus, a 2D image (B-scan) covering the vessel tissue surrounding the sensing head around 360° in an azymuthal direction may be formed from the collection of A-scans.

A-scans provide one-dimensional (1D) information of vessel tissue along a radial line centered in the sensing head. The A-scan extends from the sensing element into the vessel tissue as far as the deepest focal length achievable by the synthetic aperture in the sensing head. The IVUS imaging system assembles a two dimensional display of the vessel's cross-section from a sequence of several hundred or thousands of A-scan lines occurring around the circumference of the sensing head. In order for the image to be accurate, multiple A-line scans extending radially out of the catheter's longitudinal axis are used to have a continuous 2D display. This involves complex hardware management and poses a heavy burden on data processing speed and bandwidth requirements. For example, in some embodiments up to 512 or 1024 A-scans may be used around the circumference of a sensing head in order to form a smooth 2D image of the vessel tissue. According to embodiments of an image reconstruction system disclosed herein, a reduced number of A-scans may be used to provide accurate IVUS images.

In some embodiments consistent with the present disclosure an architecture for the synthetic-aperture reconstruction system used to produce images from solid-state IVUS catheters is provided. This architecture provides an efficient image reconstruction algorithm, reducing hardware complexity without sacrificing image quality. Generically, circuit architectures and systems as disclosed herein may be referred to as "image reconstruction" systems. A reduction in complexity (and power dissipation) of image reconstruction systems as disclosed herein could be a factor of sixteen (16) or more, compared to current data processing architectures. This reduction in complexity facilitates new possibilities for system partitioning, such as placing the image reconstruction system inside the solid-state PIM as disclosed herein.

FIG. 1 shows an IVUS imaging system 100 according to an embodiment of the present disclosure. In some embodiments the IVUS imaging system 100 is an imaging system including a sensing head 150 having a plurality of ultrasound transducers. The plurality of ultrasound transducers in sensing head 150 may form an array of transducer elements (e.g., 16, 32, 64, 96, 128, or other suitable number) arranged along a circumference centered on the longitudinal axis of catheter 102 (Z-axis in FIG. 1). In some embodiments, an IVUS imaging system may include a solid state IVUS catheter 102, a patient interface module (PIM) 104, an IVUS control system 106, and a monitor 108 to display the IVUS images generated by IVUS control 106. Solid state catheter 102 may include sensing head 150 near the distal end, according to some embodiments. In some embodiments, a portion of solid state catheter 102 may extend beyond sensing head 150 to form the tip of solid state catheter 102. PIM 104 implements the appropriate interface specifications to support solid state catheter 102. According to some embodiments, PIM 104 generates a sequence of transmit trigger signals and control waveforms to regulate the operation of the ultrasound transducers in sensing head 150.

Embodiments of an image reconstruction system as disclosed herein are sufficiently compact to be incorporated into a solid-state PIM 104. Thus, some embodiments of IVUS imaging system 100 may include a general purpose control system 106 operating as a "hub" hosting a plurality of peripheral devices. Each peripheral device may have its own application-specific interface, such as solid state PIM 104, attached. The peripheral PIMs may provide 2D reconstructed images and/or other data to "hub" control system 106, which displays the images or other data and/or performs more detailed image/data processing.

Embodiments of a reconstruction system as disclosed herein also accommodate a sensing head 150 including larger arrays of transducers operating at a faster frequency rate. For example, some embodiments may include arrays having up to 96 to 128 transducer elements. Such transducer elements may improve IVUS image quality due to the better spatial resolution provided by the larger number of transducer elements. Moreover, embodiments disclosed herein enable operation of transducer arrays in sensing head 150 at a faster frequency rate.

The array of transducer elements in sensing head 150 transmits ultrasound signals to the tissue of interest after receiving trigger signals from PIM 104. Ultrasound transducers in sensing head 150 also convert echo signals received from the tissue into electrical signals to be processed by PIM 104. PIM 104 also supplies high- and low-voltage DC power supplies to support operation of IVUS solid state catheter 102. In some embodiments, PIM 104 delivers a DC voltage to circuitry driving the transducers in sensing head 150.

FIG. 1 also illustrates a 3-dimensional (3D) coordinate system XYZ oriented with the Z-axis along the longitudinal direction of solid state catheter 102. Coordinate axes consistent with FIG. 1 are used throughout the present disclosure. One of ordinary skill will recognize that the particular choice of coordinate axes is not limiting of embodiments consistent with the present disclosure.

In embodiments of IVUS system 100 having a control system "hub", a plurality of solid state PIM's 104 may share common hardware in control system 106. In some embodiments, modality specific hardware may be located at a peripheral solid-state PIM 104. Such system architecture may be referred to as "hub and spokes" system. In some embodiments, control system 106 manages display 108 and user interface elements that are common to different instrument modalities. Furthermore, image reconstruction systems as disclosed herein are specific to each instrument modality in PIM 104 in some embodiments. Embodiments consistent with the present disclosure enable delivery of reconstructed A-scan image data in a digital format at a useable data rate, directly from solid-state PIM 104 to host control system 106. In control system 106 the A-scan image data is scan-converted and displayed as a 2D tissue image (e.g., a cross-sectional image).

Figure 2:
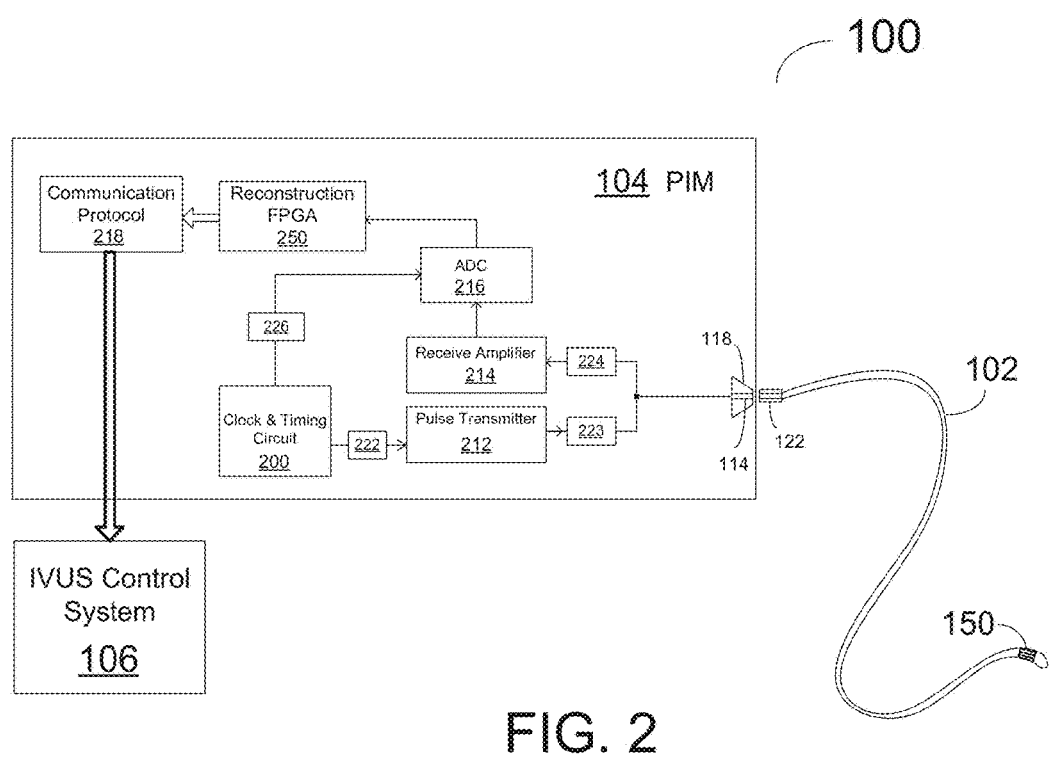
FIG. 2 shows a partial schematic view of a solid state Patient Interface Module (PIM) for use in an IVUS imaging system, according to some embodiments of the present disclosure.

FIG. 2 shows a partial view of a Patient Interface Module (PIM) 104 for use in an IVUS imaging system 100, according to some embodiments of the present disclosure. FIG. 2 illustrates PIM 104 in more detail, including a reconstruction Field-Programmable Gate Array (FPGA) circuit 250 to provide image-reconstructed data to communication protocol circuit 218, from a digital signal provided by Analog-to-Digital Converter (ADC) circuit 216. According to some embodiments, a reconstruction system is included in reconstruction FPGA 250. FPGA 250 includes a memory circuit to store data and commands, and a processor circuit to perform the commands using the stored data, and data received from ADC circuit 216. According to some embodiments, FPGA 250 includes a buffer memory to temporarily store data provided by ADC circuit 216, while processor circuit performs operations related to different data portions.

FIG. 2 illustrates a shaft 114 attached to a solid state PIM 104 by a connector 118 that fits into a telescope 122. Telescope 122 allows the length of solid state catheter 102 to be adjusted. PIM 104 also includes a pulse transmitter circuit 212 to provide a plurality of pulse signals 223 to transducers in sensing head 150. Transducers in sensing head 150 transmit electrical signals 224 to a receive amplifier circuit 214. Electrical signals 224 are amplified by receive amplifier 214. According to some embodiments, electrical signals 224 are analog signals including echo responses from the vessel tissue as detected by the transducers in sensing head 150. Analog-to-digital converter (ADC) 216 converts an amplified signal from amplifier 214 into a digital signal transferred out of PIM 104 to IVUS control system 106 by communication protocol circuit 218.

Clock and timing circuit 200 provides transmitter timing signal 222 to pulse transmitter 212 and provides digitizing signal 226 to ADC circuit 216 using a stable system clock. In some embodiments, signals 222 and 226 are synchronous to one another. Accordingly, in some embodiments transmitter timing signal 222 and digitizing signal 226 have the same phase, or their relative phase is fixed in time to within the resolution of clock and timing circuit 200. In some embodiments, clock and timing circuit 200 includes a phase-locked loop (PLL) or a frequency-locked loop (FLL) that generates signals 222 and 226 having a frequency that is a rational fraction of one another.

Embodiments consistent with the present disclosure may include different types of transducer in sensing head 150, for example traditional PZT devices, piezo-electric micro-machined ultrasonic transducer (PMUT) devices, capacitive micro-machined ultrasonic transducer (CMUT) devices, and/or combinations thereof. In some embodiments, clock and timing circuit such as 200 and reconstruction FPGA 250 is included in a modality of PIM 104 using optical techniques, such as intravascular optical coherence tomography (OCT) imaging. In the case of OCT imaging, the transducer may include an optical fiber, a filter element or some other spectrally dispersive optical component, and a photo-detector.

According to some embodiments, reconstruction FPGA 250 may use an external memory to store the collected data in PIM 104. Some embodiments of reconstruction FPGA 250 use simplified data processing schemes such that a memory circuit included in reconstruction FPGA 250 is sufficient to perform the data processing operations. Thus, in some embodiments a solid-state PIM 104 having a reduced number of external links supports solid-state IVUS catheters 102. In some embodiments, PIM 104 supports solid state catheter 102 having a sensing head 150 including up to 128 transducer elements, each operating with a center frequency of about 20 MHz (1 MHz=106 Hz), up to about 30 MHz.

In some embodiments, reconstruction FPGA 250 in PIM 104 is configured to produce gray-scale A-scan data including interpolation operations between different A-scan lines. Scan conversion and display is performed in IVUS control system 106. According to some embodiments, a grey-scale computation of A-scan lines combines data from multiple closely-spaced A-scan lines. The magnitude of the data points in the A-scan lines is averaged using an accumulator and a median filtering using minimum and maximum value filtering. A gray-scale computation includes forming a logarithmic scale of the averaged magnitude values. The logarithmic values obtained in the gray-scale computation are distributed in bins, with a certain color level assigned to each bin, forming a "grey-scale" value for each point in a 2D image formed by the A-scans. In some embodiments, native baseband A-scan data is performed in PIM 104 and A-scan interpolation and grey scale conversion is performed in IVUS control system 106.

According to some embodiments, communication protocol circuit 218 uses a relatively low bandwidth link to IVUS Control System 106. For example, in some embodiments a communication bandwidth of 8-12 Mbytes/sec between communication protocol circuit 218 and IVUS control system 106 is used. Embodiments using low bandwidth for the link between PIM 104 and IVUS control system 106 are suitable for a "hub and spokes" system architecture. Indeed, a broad bandwidth communication protocol circuit in IVUS control system 106 can accommodate a large number of PIMs 104, each having low communication bandwidth requirements.

Figure 3:
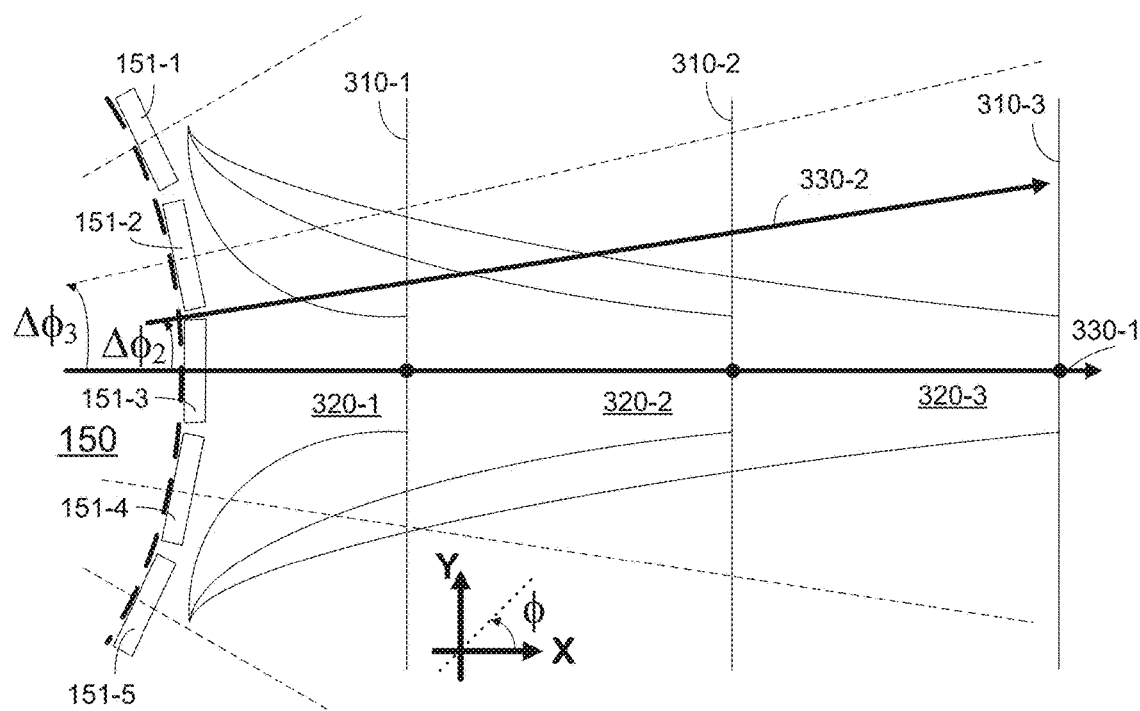
FIG. 3 shows a partial diagrammatic view of a sensing head and an array of transducer elements generating ultrasound beams, according to some embodiments of the present disclosure.

FIG. 3 shows a partial view of a sensing head 150 and an array of transducer elements 151-1, 151-2, 151-3, 151-4, and 151-5 (collectively referred to as transducer elements 151) generating ultrasound beams according to some embodiments. According to some embodiments, ultrasound transducers 151 form a synthetic aperture projecting ultrasound beams 320-1, 320-2, or 320-3 (collectively referred to as beams 320) radially outwards from catheter 102. In some embodiments, the synthetic aperture is created by triggering a group of transducer elements in sensing head 150 simultaneously, or in phase. Further according to some embodiments, a synthetic aperture in sensing head 150 generate an ultrasound beam when a group of transducer elements is triggered with a well defined phase difference between one another.

The phase difference between each of transducer elements 151 in the synthetic aperture is selected such that the ultrasound beam is focused at a pre-selected focal zone 310-1, 310-2, or 310-3 (collectively referred to as focal zones 310). While FIG. 3 illustrates three focal zones 310, one of ordinary skill would recognize that more focal zones 310 may be used in each direction selected. Some embodiments may use ten (10), sixteen (16), twenty (20), or even more focal zones for each A-scan line. In some embodiments, a single focal zone or two focal zones 310 may be used. The phase difference between transducer elements 151 in a synthetic aperture defining a focal zone 310 may be created electronically by providing suitably delayed trigger signals to each of transducers 151. The arrangement of electronic trigger pulses, time-delayed to form a focal zone 310 is referred to as an "electronic lens." An electronic lens may be created in clock and timing circuit 200 and pulse transmitter circuit 212 (cf. FIG. 2).

In some embodiments the phase difference between transducer elements 151 in a synthetic aperture is selected such that the ultrasound beam is generated at a pre-determined azymuthal angle, $\phi$, about a radial direction. Each of the pre-selected directions may be referred to as a "flavor." For example, a radial direction may be defined by the normal to the curvature of the cross section of sensing head 150 in the middle portion of the synthetic aperture, corresponding to element 151-3 (X-axis in FIG. 1). Thus, adjusting the relative phase between transducers 151, an ultrasound beam may be focused in focal zones 320 along a radial direction 330-1. In some embodiments, by adjusting the relative phase between elements 151 an ultrasound beam is formed along a "flavor" 330-2 along an azymuthal direction $\Delta\phi 2$. Azymuthal direction $\Delta\phi 2$ subtends an angle substantially half the angle $\Delta\phi 3$ formed between two adjacent transducer elements 151. According to some embodiments, angle $\Delta\phi 3$ may be about 0.1 radians; thus, angle $\Delta\phi 2$ may be about 0.05 radians. An A-scan along radial direction 330-1 ($\Delta\phi=0$) may be referred to as base-band A-scan.

Embodiments as disclosed herein include a compact and accurate method for storing focusing and flavor information. A scheme based on multiple focal zones 310 and multiple flavors relies on storing phase information for each transducer element 151 within a synthetic aperture. Phase values are stored for each flavor along the different focal zones used in an A-scan in some instances. For example, the relative phase between an acoustic front from element 151-1 and an acoustic front from element 151-2 in flavor 330-1 depends on the value $(x-f)2$ for a focal zone centered at a distance, f, from sensing head 150 at a point along line 330-1 (X-axis). The relative phase between an acoustic front from element 151-1 and an acoustic front from element 151-2 may vary also as a function of a value $(x'-f)2$, where x' is a distance from sensing head 150 along a line forming an angle $\Delta\phi 2$ with the X-axis, for flavor 330-2.

In some embodiments, storing phase values for each flavor along the different focal zones used in an A-scan is simplified by storing the first difference of the phase values. In such embodiments, for every two values of the phase a single number is stored, namely the difference between two consecutive phase values. The phase difference is stored in an accumulator register in reconstruction FPGA 250 in some implementations. Thus, the phase value at each point along a line defining the flavor scan can be computed using the accumulator, provided an initial phase value is also stored.

In some embodiments a further storage simplification is obtained by using the second difference of the phase values. In such embodiments, for every three phase values a single number is stored, namely the second difference between a first, a second, and a third phase values. For example, the second difference may result from subtracting a difference between the second phase value and the first phase value from the difference between the third phase value and the second phase value. Thus, the phase value at each point along a line defining the flavor scan is calculated using two accumulators in reconstruction FPGA 250. A first accumulator stores a difference between phase values, and a second accumulator stores a difference between values in the first accumulator. In some embodiments, a second difference method as described above enables a focus map for four (4) different flavors in a sensor head including 128 transducer elements to be stored in about 32 kBytes of memory. Such embodiments having 128 (transducers)×4 (flavors)=512 A-scan lines around solid state catheter 102 may provide better than 1 degree phase accuracy throughout the field of view.

Figure 4:
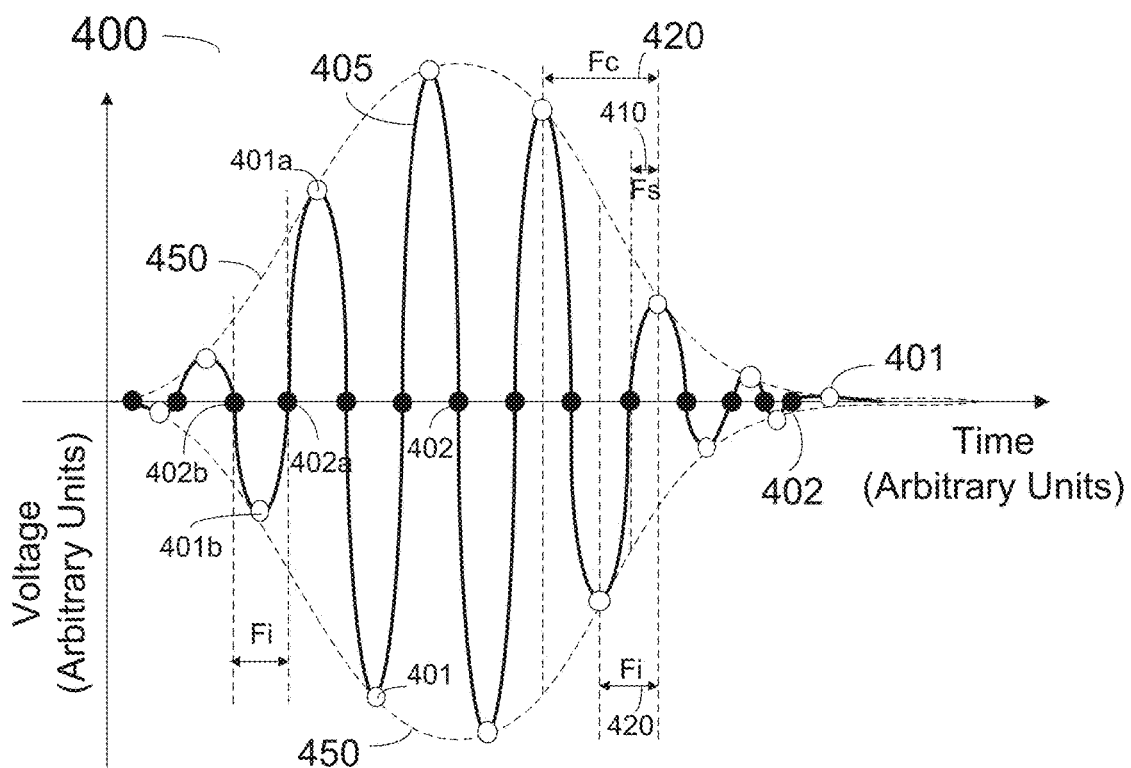
FIG. 4 shows a partial view of a digital quadrature sampling at four times transducer frequency (4×DQS) method for processing a signal, according to some embodiments of the present disclosure.

FIG. 4 shows a partial view of a 4×DQS 400 method for processing a signal 405 received in a transducer element according to some embodiments of the present disclosure. Acoustic signal 405 represents a voltage value after amplification by receive amplifier 214 (cf. FIG. 2). The voltage value in the ordinate of FIG. 4 is given in arbitrary units. The abscissa axis in FIG. 4 represents time, in arbitrary units. Signal 405 may be the echo signal received by a transducer element in sensing head 150, after the transducer element has produced an acoustic impulse having a frequency band around a center frequency Fc. The center frequency Fc may be a resonance frequency of the transducer element. Center frequency Fc may be selected to improve the performance of an image reconstruction system as disclosed herein. For example, Fc may be 20 MHz or higher, up to 30 MHz. The frequency band of a transducer element in sensing head 150 may be about 25% and up to about 50% of Fc. For example, in embodiments where Fc is 20 MHz the frequency band of a transducer element may include frequencies from 15 MHz up to 25 MHz.

FIG. 4 also illustrates an envelope 450 modulating the amplitude of signal 400. Envelope 450 results from an elastic response to the acoustic impulse induced in the vessel tissue in some embodiments. Sampling method 4×DQS 400 in FIG. 4 includes sampling points 401 and 402. Sampling points 401 and 402 may be digitization points selected by ADC circuit 216 (cf. FIG. 2) according to digitizing signal 226 provided by clock and timing circuit 200. According to some embodiments, sampling points 401 are interleaved in time with sampling points 402. That is, each of sampling points 401 is preceded by a sampling point 402. Likewise, each of sampling points 402 is preceded by a sampling point 401, according to some embodiments. Thus, approximately one half of all sampling points are points 401, and approximately one half of all sampling points are points 402. Further according to some embodiments, the interleaving of sampling points 401 and 402 is performed by reconstruction FPGA 250, using digital values comprising points 401 and 402, provided by ADC circuit 216.

To obtain best fidelity of ultrasound reconstruction, ADC circuit 216 selects sampling points 401 and 402 at a sampling frequency Fs higher than the maximum frequency expected from echo signal 400. According to some embodiments, Fs, may be higher than twice the maximum frequency expected in echo signal 405. For example, in embodiments where echo signal 400 is centered at Fc~20 MHz, the sampling frequency Fs may be 80 MHz. More generally, in embodiments where the transducer produces a narrow bandwidth ultrasound spectrum centered at frequency Fc, a sampling frequency Fs may be selected as Fs~4×Fc. Thus, according to embodiments consistent with the present disclosure, method 4×DQS 400 separates interleaved sampling points 401 and 402 such that points 401 more or less overlap with peaks and troughs of signal 400, while points 402 more or less overlap with node values of signal 405 (at zero voltage). In some embodiments, a sampling point 402 may lag from a sampling point 401 by a phase difference of about 90° in a digitizing signal 226 provided by clock and timing circuit 200.

By interleaving the digitization points provided by ADC circuit 216 into sampling points 401 and 402, reconstruction FPGA 250 operates at approximately ½ the frequency of ADC circuit 216. This reduces the load requirement and the processing capability of reconstruction FPGA 250. For example, when Fc is selected at approximately 20 MHz and Fs is selected at approximately 80 MHz, FPGA 250 can operate at a frequency Fi approximately equal to 40 MHz. Embodiments of FPGA 250 consistent with the present disclosure offer the advantage that, while FPGA 250 operates at ½ the frequency of ADC circuit 216, no phase information is lost in the data and fidelity is improved. The reason for this is the use of a quadrature procedure (I/Q) combining sampling points 401 and 402 to form complex values. For example, points 401a, 401b, 402a, and 402b may be arranged into two complex numbers c1 and c2:

$$c1 = V401a + i\ V402a,\quad (1)$$

$$c2 = -V401b - i\ V402b,\quad (2)$$

where V401a, V402a, V401b, and V402b are voltage values corresponding to sampling points 401a, 401b, 402a, and 402b, respectively. In some embodiments, 4×DQS 400 results in complex pairs (c1, c2) for each cycle of signal 405 encompassing frequency Fc. For example, complex values c1 and c2 may carry information of a peak, a trough, and two consecutive nodes in the signal having frequency Fc.

In some embodiments, use of method 4×DQS 405 provides the ability to accurately determine the phase of echo signal 400 at frequency Fc by adjusting an overall phase θ to digitizing signal 226 in clock and timing circuit 200. Thus, for example, by adjusting the phase θ, a value of the real parts Re(c1) and Re(c2) of c1 and c2 may be maximized, while a value of the imaginary parts Im(c1) and Im(c2) may be minimized for a value θo. Thus, θo determines the phase of echo signal 405 at frequency Fc. For sufficiently narrow band transducers, the phase of an echo signal slightly off of center frequency Fc may also be determined by θo.

Thus, in some instances the fidelity of image reconstruction according to method 4×DQS 400 is as good as the precision of clock and timing circuit 200, which typically operates at a high sampling frequency (e.g. 80 MHz) and the sensitivity to find minima and maxima of the real and imaginary parts of c1 and c2 (cf. Eqs. 1 and 2). In some embodiments, the precision of signal reconstruction according to 4×DQS 400 is much better than the 80 MHz frequency of clock and timing circuit 200, since a phase shift of a fraction of the clock period may result in a noticeable change in c1 and c2 (cf. Eq. 1, 2 and FIG. 4). Thus, a reconstruction FPGA 250 operating at only 40 MHz reproduces ultrasound echo signals with a precision of about 1 ns or less, according to embodiments consistent with the present disclosure. In embodiments where Fs is about 80 MHz, method 4×DQS 400 offers at least a two-fold improvement over traditional digitization schemes that would require an ADC circuit operating at least at 200 MHz to obtain a timing precision of a few ns, or about 1 ns. According to some embodiments, method 4×DQS 400 is performed by reconstruction FPGA described in detail below, in relation to FIG. 5.

Figure 5:
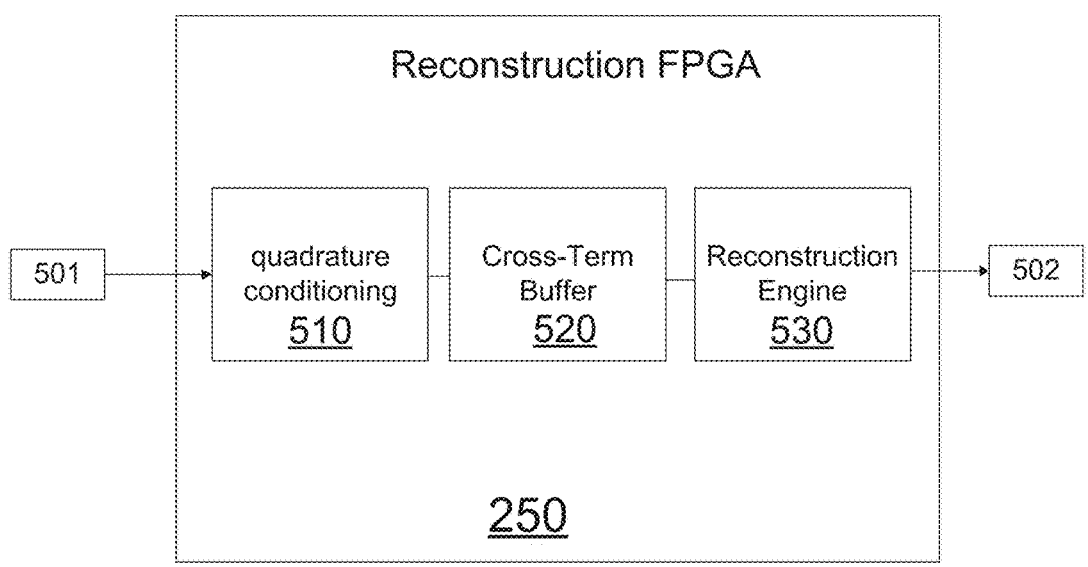
FIG. 5 shows a partial block diagram of a reconstruction Field-Programmable Array (FPGA) circuit for image reconstruction, according to some embodiments of the present disclosure.

FIG. 5 shows a partial block diagram of a reconstruction FPGA circuit 250 for image reconstruction according to some embodiments of the present disclosure. Reconstruction FPGA 250 may include an I/Q internal conditioning circuit 510, a cross-term buffer circuit 520, and a reconstruction engine circuit 530. According to some embodiments, input data 501 includes digital data sampled by ADC circuit at a frequency Fs. In some embodiments consistent with method 4×DQS 400, frequency, Fs, is approximately Fs~4×Fc, as discussed above. For example, Fs for input signal 501 may be 80 MHz, in embodiments where the transducer Fc is about 20 MHz. Output data 502 includes interleaved I/Q pairs such as values c1 and c2 (cf. Eqs. 1 and 2 above) at a reduced frequency Fi. For example, in some embodiments the value of Fi may be Fi~½ Fs. For Fs approximately equal to 80 MHz, then output 502 may operate at approximately 40 MHz.

In some embodiments, I/Q internal conditioning circuit 510 transforms digital input 501 into a complex baseband formed by values c1 and c2 (cf. Eqs. 1 and 2). In some embodiments, I/Q internal conditioning circuit 510 performs method 4×DQS 400 to provide complex data c1 and c2, as described in detail above (cf. FIG. 4). Cross-term buffer circuit 520 provides a two- or four-line buffer to support averaging of the c1 and c2 values provided by I/Q internal conditioning circuit 510. In some embodiments, cross-term buffer circuit 520 is used as a "ping-pong" memory to adjust the data rate between acquisition of input signal 501 and reconstruction in output signal 502.

Reconstruction FPGA 250 includes reconstruction engine 530 that processes the I/Q conditioned data as buffered and averaged by cross-term buffer 520. Reconstruction engine 530 processes the I/Q pairs (e.g. c1 and c2 above) by flavor, with each flavor sharing a common set of focus parameters (cf. FIG. 3).

Figure 6:
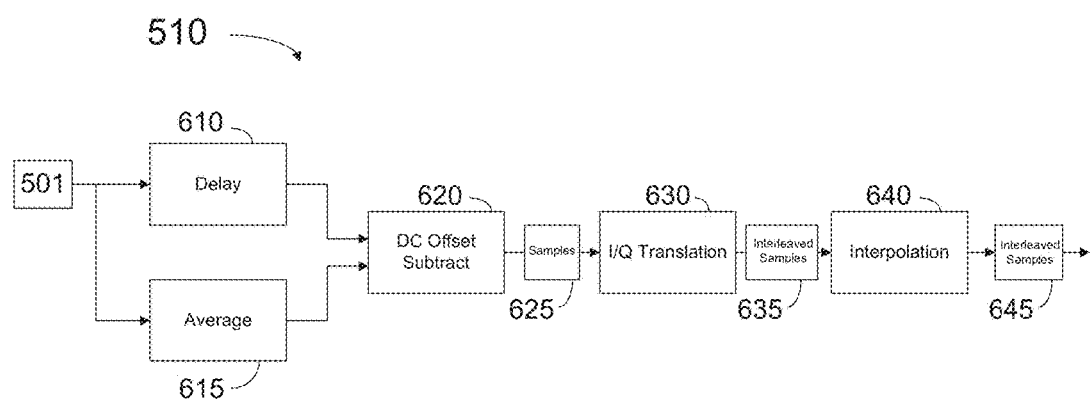
FIG. 6 shows a partial diagram of an I/Q internal conditioning circuit for digital signal processing, according to some embodiments of the present disclosure.

FIG. 6 shows a partial diagram of an I/Q internal conditioning circuit 510 for digital signal processing according to some embodiments. Conditioning circuit 510 includes delay circuit 610, averaging circuit 615, offset subtract circuit 620, I/Q translation circuit 630, and interpolation circuit 640. Input signal 501 including digital samples from ADC circuit 216 are used by averaging circuit 615 to compute a DC offset for the data. A total number of N sample points is received from input signal 501 for a given data processing cycle. Delay circuit 610 introduces a delay on approximately one half of the N sample points received from signal 501. For example, in some embodiments data points 401 may be delayed with respect to data points 402 so that the real and imaginary parts of complex values c1 and c2 overlap in time (cf. FIG. 4 and Eqs. 1 and 2). One of regular skill may recognize that the total number of sampling points, N, is not limiting. In some embodiments, a number N of 1000 points may be used per each A-scan line. Some embodiments may use a higher number of points, such as N=1500, or more.

Circuit 620 subtracts from the N data points the DC offset obtained by average circuit 615. As a result, samples 625 at frequency Fs are transferred to I/Q translation circuit 630. I/Q translation circuit 630 forms complex pairs c1 and c2 for every cycle of an Fc waveform. I/Q translation circuit 630 uses Eqs. 1 and 2 to form complex numbers c1 and c2 in some implementations. In some embodiments I/Q translation circuit 630 changes the sign on the third and fourth samples in every four consecutive samples 625, interpreting the first and third samples as "I" components (e.g. samples

401 in FIG. 4), and samples 2 and 4 as "Q" components (e.g. samples 402 in FIG. 4). According to some embodiments, c1 and c2 samples are interleaved at a frequency Fi approximately one half the sampling frequency, Fi~½×Fs. Thus, interleaved samples 635 are transferred at a frequency Fi to interpolation circuit 640. According to some embodiments, for applications in which Fs is approximately equal to 80 MHz, Fi may be approximately 40 MHz.

Interpolation circuit 640 includes a filter for attenuating signal frequencies lower than Fi and higher than Fi. Interpolation circuit also applies a phase delay between "I" samples (e.g. samples 401) and "Q" samples (e.g. samples 402) to a common sample time. In some embodiments the output of interpolation circuit 640 is interleaved samples 645 formed as I/Q pairs. Interleaved samples 645 include complex values c1 and c2, where each of c1 and c2 values includes an "I" and a "Q" component, synchronous to one another.

Figure 7:
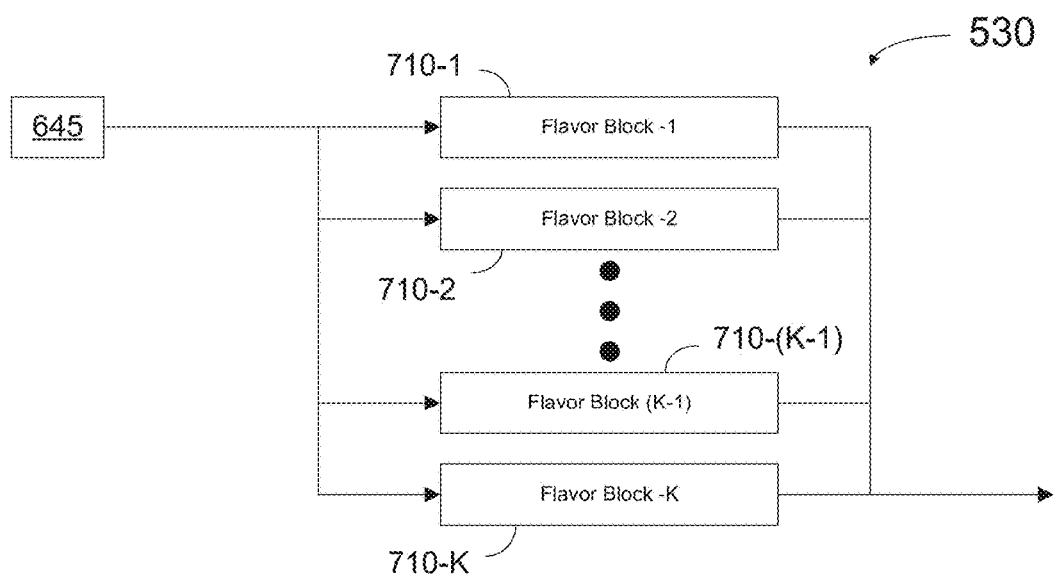
FIG. 7 shows a partial diagram of a reconstruction engine for image reconstruction, according to some embodiments of the present disclosure.

FIG. 7 shows a partial view of a reconstruction engine 530 for image reconstruction, according to some embodiments. Reconstruction engine 530 receives interleaved I/Q pairs 645 from I/Q internal conditioning circuit 510 after buffering in circuit 520. I/Q pairs 645 have a frequency Fi. Reconstruction engine 530 separates I/Q pairs 645 according to flavor, into flavor blocks 710-1, 710-2, through 710-K (collectively referred to as flavor blocks 710). The number of flavors, K, is not limiting, and different embodiments may use different number of flavors per each synthetic aperture. The number of flavors used, K, between adjacent transducers of a transducer array depends on the resolution desired for the IVUS imaging system in some instances. In some embodiments K may be eight (8), or less. In some embodiments K may be four (4), or even two (2). The data processing and components in each flavor block 710 is described in detail below in relation to FIG. 8.

Figure 8:
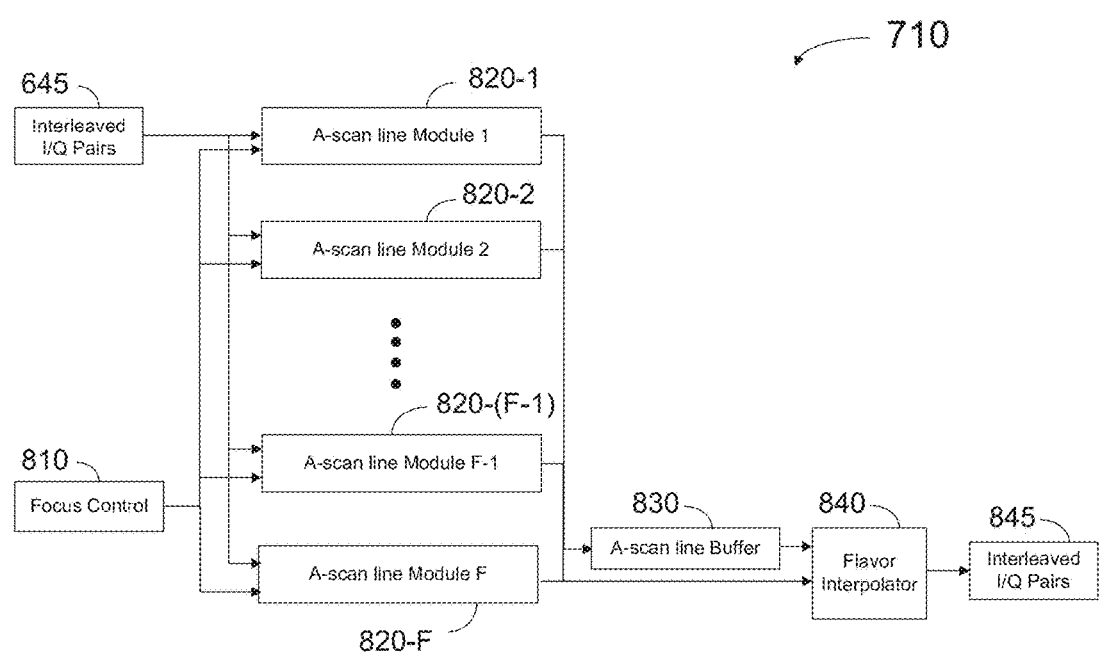
FIG. 8 shows a partial diagram of a flavor block for image reconstruction, according to some embodiments of the present disclosure.

FIG. 8 shows a partial view of a flavor block 710 according to some embodiments. Flavor block 710 receives interleaved I/Q pairs 645 and using information from focus control circuit 810, flavor block 710 reconstructs A-scan lines in A-scan line modules 820-1, 820-2, through 820-F (collectively referred to as A-scan line modules 820). A-scan line modules 820 may reconstruct base-band A-scans for each of the synthetic apertures used around sensing head 150. A baseband A-scan may be as scan line 330-1, described in detail above (cf. FIG. 3). The number of synthetic apertures, F, used to collect an entire 2D frame around sensing head 150 may be 64, 128, or a larger number. In some embodiments, a synthetic aperture may be centered on each of the transducer elements 151 included around sensing head 150. In such embodiments, a base-band A-scan may be produced for each of the transducers. Thus, for sensing head 150 having 64 transducer elements 151, a number F=64 of base-band A-scans may be performed. Likewise, for sensing head 150 having 128 elements, a number F=128 of base-band A-scan lines may be formed.

Focus control circuit 810 stores focus information to be processed by each of A-scan modules 820. According to some embodiments, focus control circuit 810 includes a first accumulator storing phase difference information for each focal zone 310 along baseband A-scan line 330-1 (cf. FIG. 3). In some embodiments, focus control circuit 810 includes a second accumulator storing second phase difference information for each focal zone 310 along baseband A-scan line 330-1.

FIG. 8 also shows an A-scan line buffer circuit 830 which stores the information of A-scan line modules 820 for processing in a flavor interpolator circuit 840. Flavor interpolator circuit 840 interpolates values between A-scan lines provided by buffer 830 to obtain signal values at positions corresponding to the flavor in flavor block 710. For example, the flavor being computed in flavor interpolator circuit 840 may be as flavor 330-2, forming an angle $\Delta\phi 2$ with baseband A-scan 330-1 (along the X-axis, cf. FIG. 3). According to some embodiments, flavor interpolator circuit 840 uses a first value of a signal, including phase, along base-band A-scan 330-1 and a second value of a signal, including phase, along an adjacent baseband A-scan, to obtain the value of a signal along flavor 330-2. An adjacent A-scan may correspond to element 151-2, forming an angle $\Delta\phi 3$ with base-band A-scan line 330-1 (cf. FIG. 3).

According to some embodiments using flavor block 710 as described above, a reduced number of flavor blocks, K, are necessary in reconstruction engine 530 (cf. FIG. 7). For example, in some embodiments only one (K=1) or two (K=2) flavor blocks are used. Such embodiments provide a 4- to 8-fold reduction in memory and computing resources in reconstruction FPGA 250 compared to instances using 4, 8, or more flavors. Thus, in embodiments using flavor interpolator circuit 840 combined with method 4×DQS 400 (cf. FIG. 4), a net simplification by a factor of 8- to 16- is obtained. The above simplification is a consequence of live scan reduction through flavor interpolation, and also a factor of ~2 reduction in the frequency of operation of method 4×DQS 400 method discussed above (cf. FIG. 4).

In some embodiments, flavor interpolator circuit 840 is used to calculate eight flavors, interpolating two flavors obtained by A-scan lines such as 330-1 and 330-2 (cf. FIG. 3).

It is recognized that some or all of the "flavors" in reconstruction engines consistent with the present disclosure can be produced by simple interpolation between baseband A-scans including phase. Phase information stored as described in relation to FIG. 3 above is maintained in I/Q pairs 645 (c1 and c2), enabling the accurate reconstruction of a 2D image. Interpolating baseband A-scans (including phase) retains the linearity of the delay-and-sum reconstruction process, so that the interpolation can accurately calculate the intermediate A-scans (flavors) between fully-reconstructed scan lines. In some embodiments, the spatial sampling of base-band A-scans is selected to produce precise image reconstruction.

Interpolation between scan lines (or even spatial filtering over several scan lines) is simpler than adding more flavors to reconstruction engine 530. The reduction in complexity becomes more pronounced as the number of array elements 151 in sensing head 150 is increased. Eliminating the reconstruction of multiple flavors enables a substantial reduction in hardware and computational complexity of IVUS system 100. This includes a reduction in power consumption for FPGA 250, which houses reconstruction engine 530.

In some embodiments, four flavors are calculated to provide a 256-line image from 64 base-band A-scans. Each flavor that is interpolated using interpolator 840 reduces a requirement for reconstruction in terms of data memory, focus memory, and DSP hardware. Reducing reconstruction engine 530 from eight flavors to one flavor may thus provide an eight-fold savings in memory, and an eight-fold reduction in clock speed or number of processing channels used.

The interpolation hardware in flavor interpolator 840 is a small overhead compared to the reconstruction hardware for "native" A-scans obtained directly from echo signal 405. For example, a method for image reconstruction using two flavors (K=2, cf. FIG. 7) combined with a 2-fold simplification of data processing by method 4×DQS 400—e.g. 200 MHz to 80 MHz sampling speed—provides an 8-fold reduction in complexity over existing techniques.

In some embodiments, flavor interpolator 840 uses a linear interpolation of I and Q components (sampling points 401 and 402 in FIG. 4, respectively). In some embodiments, flavor interpolator 840 uses a Magnitude/Phase interpolation that is more accurate but slightly more complex to implement. Some such embodiments use an interpolation of the magnitude, MAG, of values c1 and c2 (cf. Eqs. 1 and 2) and their phase, PHAS, as follows:

$$MAG = \sqrt{I^2 + Q^2} \qquad (3)$$

$$PHAS = \text{Arc Tan}(Q/I) \qquad (4)$$

where I=402a, or I=−402b; and Q=401a, or Q=−401b; (cf. Eqs. 1 and 2).

In some embodiments, flavor interpolator 840 uses a small FIR filter (spatial low-pass filter) to perform smoothing between adjacent baseband A-scans.

In some embodiments, flavor interpolator 840 is implemented with as few as 24 digital signal processing (DSP) slices and 48 memory blocks for a one-flavor scheme. In some embodiments, 48 DSP slices and 96 memory blocks are used in a two-flavor scheme. Some embodiments include a favorable tradeoff between the number of DSP slices and a clock speed (e.g., 80 DSP slices for the two-flavor option) in clock and timing circuit 200. Thus, some embodiments increase DSP slices and reduce clock speed.

Embodiments of image reconstruction as disclosed herein are desirable in view of current hardware enhancements. For example, a 128-element array uses approximately double the resources as a 64 array in sensing head 150. The clock rate increases correspondingly for a higher frequency array. With an architecture for image reconstruction as disclosed herein, the entire reconstruction engine for a 128-element array could fit within a single Spartan-6 FPGA (up to 180 DSP slices and 268 memory blocks) or a series 7 family device (Artix/Virtex) operating at a modest clock rate (<100 MHz).

Adjacent flavors (between two elements) are composed of linear combinations of exactly the same echo signals (cross-terms) as one another. The main difference between adjacent flavors is in the complex weights that are applied to the various echo signals as they are accumulated to form a synthetically focused scan line. Moving from one reconstructed scan line to the next, most of the weights and phase shifts applied to the various echo components vary only a small amount. Therefore, interpolating the weights between native scan lines provides a smooth transition from one flavor to the next. "Native" scan lines may be base-band A-scan lines or A-scan lines having a flavor. Native scan lines are obtained by collecting echo signals produced by impulses triggered on transducers 150.

In some embodiments a sensing head 150 has an aperture width of 10 wavelengths and an angular element spacing of 0.1 radians. In such embodiments, the spatial frequency bandwidth is 20 wavelength (accounting for the round-trip propagation). For a typical apodization function, most of the spatial frequency response is covered by 10 wavelengths, with only the fringes of the spatial frequency response extending out to the full 20 wavelengths spatial bandwidth. In embodiments as above, one-flavor sampling the image at only 0.1 radian increments (corresponding to the array element spacing) may be too sparse to obtain acceptable spatial resolution. Thus, more native scan flavors, such as two flavors separated by 0.05 radians, may be desirable in such embodiments, to reduce image artifacts.

Figure 9:
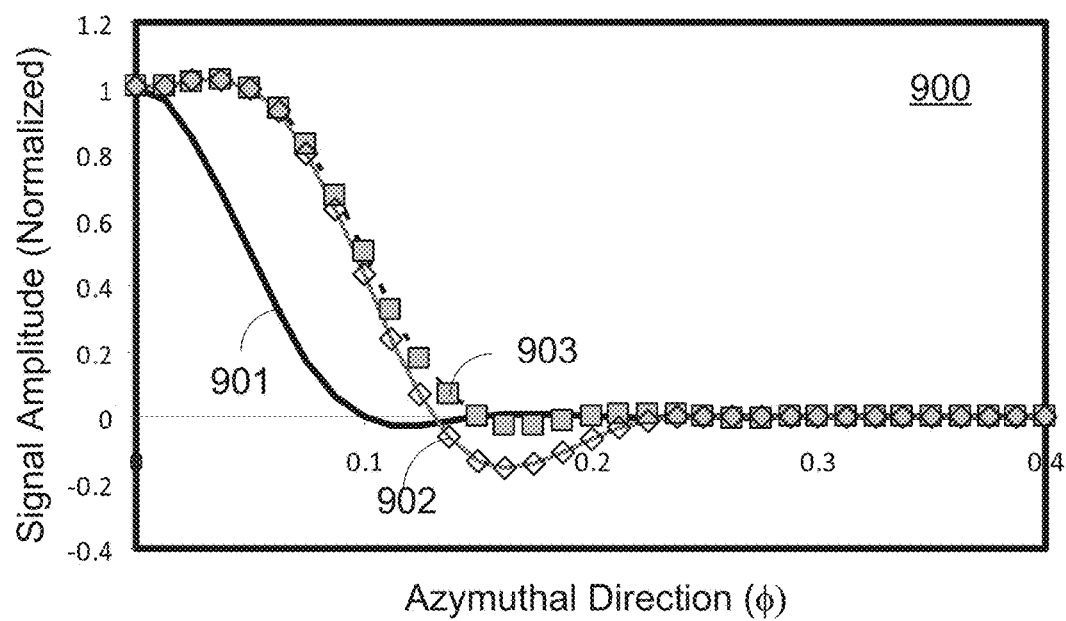
FIG. 9 shows a graph of a point-spread-function (PSF) of an acoustic signal processed according to some embodiments of the present disclosure.

FIG. 9 shows a graph 900 of a point-spread-function (PSF) of an acoustic signal processed according to some embodiments of the present disclosure. Curve 901 shows a PSF of a diffraction limited acoustic image. Curve 903 shows a PSF of an acoustic image obtained using a linear interpolation in flavor interpolator 840. Curve 902 shows a PSF of an acoustic image obtained using a four-point spatial filtering in flavor interpolator 840. The PSFs in graph 900 are obtained using Hanning weighting of the data and one flavor.

In embodiments as shown in FIG. 9, image quality may be compromised at the main-lobe width (resolution) using a linear interpolation (curve 903), or a four-point filtering (curve 902). Also, a significant increase in side lobe level with the four-point FIR filter may be appreciated. This is a tradeoff from drastically simplifying reconstruction engine 530 to a single flavor.

Figure 10:
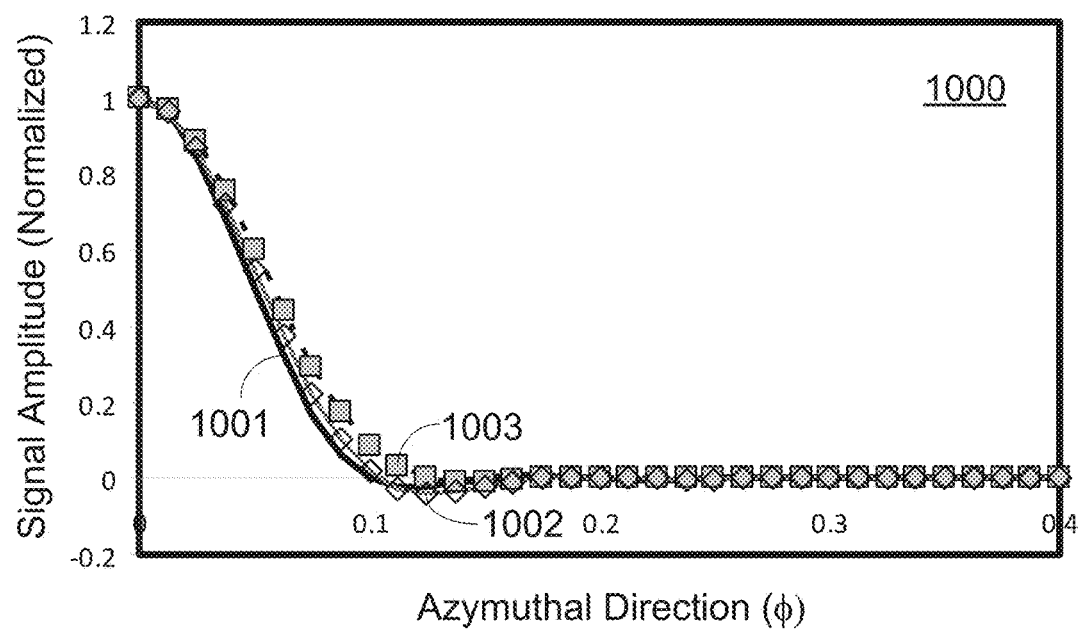
FIG. 10 shows a graph of a PSF of an acoustic signal processed according to some embodiments of the present disclosure.

FIG. 10 shows a graph 1000 of a PSF for an acoustic signal processed according to some embodiments of the present disclosure. In graph 1000, the results are obtained for image reconstruction engine 530 using Hanning weighting and two flavors. It is observed that, when an extra flavor is reconstructed to fill in the image between the elements with an angular spacing of 0.05 radians, then the image is well-sampled, and either interpolation or spatial filtering reconstructs the true image adequately. Curve 1003 shows the result of reconstruction engine 530 using a linear interpolation. Curve 1002 shows the result of reconstruction engine 530 using four-point spatial filtering on the PSF. In this case, linear interpolation causes a modest increase in main-lobe width, while a four-point FIR filter causes only a 5% degradation in resolution compared to the theoretical PSF. There are no significant increases in side lobes from either interpolation method.

Figure 11:
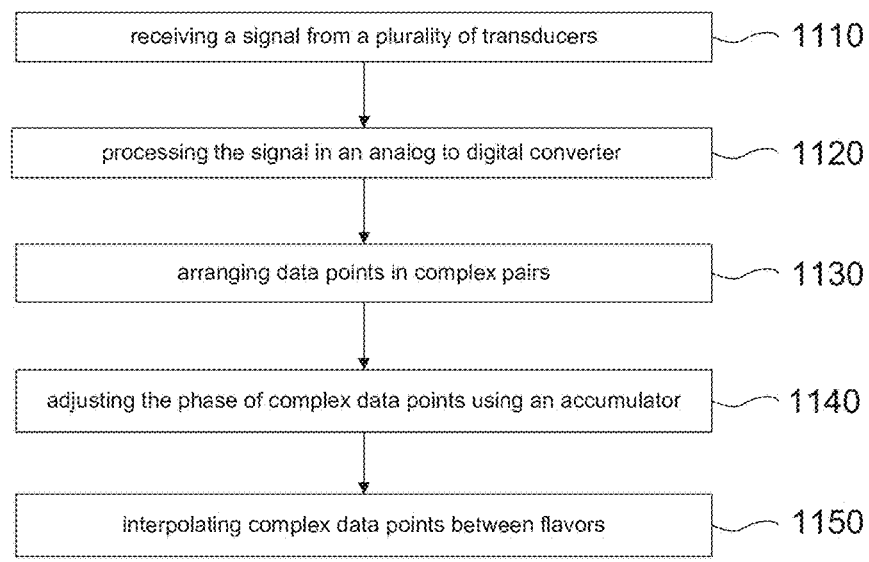
FIG. 11 shows a flowchart of a method for image reconstruction, according to some embodiments of the present disclosure.

FIG. 11 shows a flowchart of a method 1100 for image reconstruction according to some embodiments of the present disclosure. Method 1100 is performed by memory circuits and processor circuits included in FPGA 250 in some instances. In some embodiments, method 1100 is partially performed by FPGA 250, and partially performed by ADC circuit 216 and clock and timing circuit 200. Further according to some embodiments, method 1100 is partially performed by control system 106.

Step 1110 includes receiving a signal from a plurality of transducers. In step 1110, the plurality of transducers may form a synthetic aperture. In step 1110, the signal received may be an echo signal having a frequency band centered on a resonance frequency of the transducers, Fc. Step 1120 includes sampling the signal in an analog to digital converter having a digitizing frequency at least two times the center frequency Fc. Step 1120 may include processing the signal having a digitizing frequency about four times the center frequency Fc. Step 1130 includes arranging data points in complex pairs. In some embodiments, step 1130 includes interleaving the data points into two sets separated from each other by a 90° phase lag.

In step 1130, the phase of the received signal may be found by measuring voltage values in the two interleaved data sets. For example, according to some embodiments, a sum of the first interleaved data set is used and a sum of the second interleaved data set is used, while adjusting the phase of the entire data set. The value of the phase that maximizes the sum of the first interleaved data set may also minimize the sum of the second interleaved data set. This value may be the phase of an acoustic echo signal received at a frequency about one fourth (¼th) the value of the digitizing frequency. In some embodiments, the complex pairs are complex values c1 and c2 defined in Eqs. 1 and 2 above.

Step 1140 includes adjusting the phase of complex data points using an accumulator. Step 1140 may include finding a focal zone associated with the complex data point and finding the phase of the data point in relation to a flavor direction. Step 1140 may also include defining a cross term for each data point with a phase value between a tissue point and each transducer element in a synthetic aperture. Step 1150 includes interpolating complex data points between flavors. In some embodiments, step 1150 includes using a linear interpolation for real and imaginary parts of the complex data points separately. In some embodiments, step 1150 includes interpolating a magnitude value and a phase value of the complex data point using a non-linear function (cf. Eqs. 3 and 4). Step 1150 may also include the step of forming a 2D image of the vessel tissue using the interpolated values.

In some embodiments, a two-flavor reconstruction engine with a four-point FIR spatial filter as disclosed herein is used for image reconstruction with no perceptible loss in image quality, compared to an eight-flavor reconstruction. Considering the at least two-fold savings associated with method 4×DQS 400 and the four-fold reduction in flavors (from eight to two), architectures as disclosed herein provide at least an eight-fold reduction in complexity. Further reduction in complexity is realized through a compact focus memory scheme, storing phase information for the transducer elements in a synthetic aperture using a first and a second difference method, as described in detail above in relation to FIG. 3.

Digitization method 4×DQS 400 simplifies the design and operation of PIM 104. According to some embodiments method 4×DQS 400 provides a two-fold reduction in the speed requirement for data acquisition. This, added to a simplification of flavor reconstruction may provide up to an eight-fold improvement in the entire image reconstruction process. In some embodiments, PIM 104 is a solid-state PIM including a low complexity (and low power) reconstruction engine within the PIM, delivering A-scans directly to control system 106 over a low bandwidth digital link. In some embodiments, a transmission rate between PIM 104 and control system 106 for gray-scale data may be 8 Mbytes/sec. In such embodiments, scan conversion is performed in control system 106, whereas flavor interpolation is performed in PIM 104. In some embodiments, reconstructed baseband data is delivered over a 12 Mbytes/sec link between PIM 104 and control system 106, with flavor interpolation and gray-scale conversion performed in control system 106.

Embodiments of the disclosure described above are exemplary only. One skilled in the art may recognize various alternative embodiments from those specifically disclosed. Those alternative embodiments are also intended to be within the scope of this disclosure. As such, the disclosure is limited only by the following claims.

What is claimed is:

1. A system for collecting tissue images comprising:
   a patient interface module (PIM), the PIM comprising:
   a pulse transmitter circuit;
   an analog to digital converter circuit; and
   a reconstruction FPGA circuit;
   an intravascular ultrasound (IVUS) imaging catheter comprising a sensing head near the distal end, the sensing head comprising an array of transducer elements associated with an aperture configuration and configured to obtain image data while positioned within a blood vessel, wherein the array of transducer elements comprises a circumferential arrangement around the sensing head such that the aperture configuration is associated with a group of the array of transducer elements forming a portion of the circumferential arrangement, wherein the PIM is configured to process the image data obtained by the array of transducer elements; and
   a control system distinct from the PIM, wherein the control system is configured to receive the processed image data from the PIM and to output an IVUS image based on the processed image data to a display,
   wherein the PIM is communicatively interposed between the control system and the catheter,
   wherein the reconstruction FPGA circuit comprises:
   an internal conditioning circuit;
   a buffer circuit; and
   a reconstruction engine circuit, wherein the reconstruction engine circuit comprises:
   a circuit to measure a phase of a signal, wherein the circuit to measure the phase of the signal includes digitization points forming two complex numbers for each cycle of a center frequency of the signal; and
   a flavor interpolation circuit configured to form a data set separating the digitization points according to associated flavors of the aperture configuration,
   wherein the pulse transmitter circuit is configured to generate triggers for the array of transducer elements according to the associated flavors of the aperture configuration, and
   wherein the flavor interpolation circuit is configured to interpolate the digitization points according to the associated flavors of the aperture configuration.

2. The system of claim 1 wherein the array of transducer elements comprises an ultrasound transducer.

3. The system of claim 2 wherein the center frequency of the signal is a center frequency in a response spectrum of the ultrasound transducer.

4. The system of claim 1 wherein the array of transducer elements comprises at least one of a piezo-electric transducer, a piezo-electric micro-machined ultrasonic transducer (PMUT), or a capacitive micro-machined ultrasonic transducer (CMUT).

5. The system of claim 1 wherein the internal conditioning circuit is configured to provide the two complex numbers from the digitization points separated by approximately ¼ of a wave cycle of the center frequency of the signal.

6. The system of claim 1 wherein the digitization points comprise at least two nodes in the signal.

7. The system of claim 1 wherein the digitization points comprise two interleaved sets of data points in the signal.

8. The system of claim 7 wherein the two interleaved sets are separated by a pre-selected phase.

9. The system of claim 8, wherein the pre-selected phase is a ¼ wave cycle of the center frequency of the signal.

10. The system of claim 1 wherein the internal conditioning circuit further comprises:
    a delay circuit;
    an averaging circuit;
    an offset subtract circuit to subtract a signal from the averaging circuit from a signal of the delay circuit;
    an I/Q translation circuit to provide a complex number from a sample of the offset subtract circuit; and
    an interpolation circuit to interpolate complex values from the I/Q translation circuit.

11. The system of claim 1 wherein the flavor interpolation circuit is configured to select the associated flavors of the aperture configuration by collecting signals from the array of transducer elements separated by a selected phase angle between the transducer elements.

12. The system of claim 1 wherein the flavor interpolation circuit is further configured to interpolate data values from different flavors of the aperture configuration in the data set.

13. The system of claim 12 wherein the flavor interpolation circuit is configured to implement a linear interpolation.

14. The system of claim 12 wherein the flavor interpolation circuit is configured to implement a four-point finite impulse response (FIR) spatial filter.

15. The system of claim 1, wherein the array of transducer elements is configured to convert an ultrasound echo received from the tissue into a corresponding electrical signal; and wherein the circuit to measure the phase of the signal is configured to measure the phase of the electrical signal corresponding to the ultrasound echo.

16. The system of claim 1, wherein the PIM further comprises:

a timing circuit coupled to the pulse transmitter circuit and the analog to digital converter circuit, the timing circuit outputs a transmit timing signal to the pulse transmitter circuit and a digitizing signal to the analog to digital converter circuit.

17. The system of claim 16, wherein the transmit timing signal to the pulse transmitter circuit is synchronized to the digitizing signal to the analog to digital converter circuit.

* * * * *